United States Patent [19]

Collins et al.

[11] 4,438,500

[45] Mar. 20, 1984

[54] RAPID VOLATILITY ANALYZER

[75] Inventors: Michael J. Collins, Matthews; Bernard W. Cruse, Jr., Indian Trail; Ronald J. Goetchius, Charlotte, all of N.C.

[73] Assignee: CEM Corporation, Indian Trail, N.C.

[21] Appl. No.: 29,883

[22] Filed: Apr. 13, 1979

Related U.S. Application Data

[63] Continuation-in-part of Ser. No. 603,354, Aug. 11, 1975, abandoned, which is a continuation-in-part of Ser. No. 381,087, Jul. 20, 1973, Pat. No. 3,909,598.

[51] Int. Cl.³ .................... G06F 15/46; G01N 5/04
[52] U.S. Cl. .................... 364/567; 364/497; 73/76; 177/25; 374/14
[58] Field of Search ............ 364/567, 568, 497, 526, 364/900, 200, 706; 219/10.55 MR; 131/22 R, 135; 73/73, 75, 77, 76, 15 R; 177/25

[56]       References Cited
         U.S. PATENT DOCUMENTS

| Re 28,507 | 8/1975 | Rusch | 340/324 AD |
|---|---|---|---|
| 2,047,765 | 7/1936 | Brabender | 73/51 |
| 2,539,754 | 1/1951 | Rettinger et al. | 161/17 |
| 2,569,749 | 10/1951 | Dietert et al. | 34/44 |
| 2,581,204 | 1/1952 | Reilly | 99/256 |
| 2,744,990 | 5/1956 | Schroeder et al. | 219/10.55 |
| 2,765,160 | 10/1956 | Dietert et al. | 265/29 |
| 2,828,623 | 4/1958 | Benedict | 73/76 |
| 2,869,360 | 1/1959 | Stein | 73/76 |
| 2,888,543 | 5/1959 | Haagensen | 219/10.55 |
| 2,915,898 | 12/1959 | Van Luik | 73/338.3 |
| 2,993,973 | 7/1961 | Johnson et al. | 219/10.55 |
| 2,999,381 | 9/1961 | Chope et al. | 73/73 |
| 3,050,144 | 8/1962 | Rice et al. | 177/4 |
| 3,081,194 | 3/1963 | Hunsberger et al. | 117/113 |
| 3,081,429 | 3/1963 | Moe | 324/61 |
| 3,091,301 | 5/1963 | Stone | 177/1 |
| 3,178,929 | 4/1965 | Gross | 73/15.4 |
| 3,182,166 | 5/1965 | Bohm et al. | 219/10.55 |
| 3,183,710 | 5/1965 | Spang | 73/76 |
| 3,205,355 | 9/1965 | Ehlert | 250/83 |
| 3,360,985 | 1/1968 | Christian | 73/53 |
| 3,365,562 | 1/1968 | Jeppson | 219/10.55 |
| 3,447,906 | 9/1969 | Zimmerli | 23/253 |

(List continued on next page.)

FOREIGN PATENT DOCUMENTS

| 1066679 | 10/1959 | Fed. Rep. of Germany . |
|---|---|---|
| 2275766 | 6/1974 | France . |
| 44-23956 | 10/1969 | Japan . |
| 1176907 | 1/1970 | United Kingdom . |

OTHER PUBLICATIONS

Operational Amplifiers, Manual by Philbrick/Nexus Research, Copyright 1968 by Dedham, Mass. First Edition, 1st printing Dec., 1965, Second Edition, 1st printing, Jun. 1966; 2nd printing, Feb., 1968, 3rd printing, Aug., 1969.

Use of Computer Program to Correct for Sample Interaction, a Significant Adjunct to Continuous-Flow Analysis, by Ralph E. Thiers, Jule Meyn, and Robert F. Wilderman, Clinical Chemistry, vol. 16, No. 10, 1970, pp. 832–839.

*Primary Examiner*—Edward J. Wise
*Attorney, Agent, or Firm*—Herbert M. Adrian, Jr.

[57]         ABSTRACT

A rapid volatility analyzer is described, as well as a method for rapidly determining weight changes in substances containing a volatile material. In particular, there is described an apparatus which rapidly determines the percentage of volatiles in a substance which contains unknown quantities of polar volatiles such as water or moisture, solvents, plasticizers and the like. The apparatus provides rapid determinations without operator assistance other than the placing of a sample of the substance being tested on the electronic balance. The particular improvement in the present invention relates to the ability of the apparatus to project final dry weight without completely drying the test sample utilizing a short heat induction period. This improvement greatly reduces the heating time required and avoids overdrying of the test sample.

30 Claims, 2 Drawing Figures

U.S. PATENT DOCUMENTS

| | | | |
|---|---|---|---|
| 3,459,506 | 8/1969 | Finucane | 23/230 |
| 3,469,931 | 9/1969 | Boon | 8/137 |
| 3,473,175 | 10/1969 | Sieber | 8/158 |
| 3,477,274 | 11/1969 | Wald et al. | 73/15 |
| 3,493,738 | 2/1970 | Keller | 235/196 |
| 3,500,012 | 3/1970 | Hilton | 219/10.61 |
| 3,526,737 | 9/1970 | Black | 219/10.55 |
| 3,556,111 | 1/1971 | Wochnowski | 131/135 |
| 3,561,551 | 2/1971 | Susor | 177/3 |
| 3,564,224 | 2/1971 | Chope | 235/151.35 |
| 3,580,683 | 5/1971 | Schulkind | 356/184 |
| 3,593,313 | 7/1971 | Tomaszewski | 340/172.5 |
| 3,596,071 | 7/1971 | Doering | 235/151.1 |
| 3,599,161 | 8/1971 | Stoughton | 340/172.5 |
| 3,649,729 | 3/1972 | Davis et al. | 264/40 |
| 3,669,626 | 6/1972 | Thiers et al. | 23/230 A |
| 3,673,852 | 7/1972 | Davis | 73/15 |
| 3,677,064 | 7/1972 | Simpson | 73/17 R |
| 3,681,595 | 8/1972 | Dahlin | 250/83 C |
| 3,682,783 | 8/1972 | Dahms et al. | 204/1 T |
| 3,684,875 | 8/1972 | Smith et al. | 235/151.33 |
| 3,690,833 | 9/1972 | Ferrari | 23/230 R |
| 3,726,775 | 4/1973 | Dahlberg et al. | 204/158 R |
| 3,737,608 | 6/1973 | Nagao et al. | 219/10.55 |
| 3,749,657 | 7/1973 | Bras et al. | 204/181 |
| 3,749,659 | 7/1973 | Dahms et al. | 204/195 T |
| 3,777,127 | 12/1973 | Goetchius et al. | 235/151.3 |
| 3,777,258 | 12/1973 | Wochnowski | 324/61 QS |
| 3,795,099 | 3/1974 | Tsuruishi | 58/23 R |
| 3,813,918 | 6/1974 | Moe | 73/15 B |
| 3,840,025 | 10/1974 | Fowler et al. | 131/135 |
| 3,855,461 | 12/1974 | Stockwell | 235/156 |
| 3,867,273 | 2/1975 | Gilbert | 204/195 R |
| 3,875,395 | 4/1975 | Jilek | 235/183 |
| 3,890,825 | 6/1975 | Davis | 73/15 B |
| 3,909,598 | 9/1975 | Collins, et al. | 364/567 |
| 3,916,670 | 11/1975 | Davis et al. | 73/15 B |
| 3,973,431 | 8/1976 | Ginhoux et al. | 73/76 |
| 4,044,607 | 8/1977 | Deal | 73/73 |
| 4,127,232 | 11/1978 | Gagliardo et al. | 235/419 |

RAPID VOLATILITY ANALYZER

This is a continuation-in-part of Ser. No. 603,354 filed Aug. 11, 1975, now abandoned, which is a continuation-in-part of Ser. No. 381,087 filed July 20, 1973, now U.S. Pat. No. 3,909,598 issued Sept. 30, 1975.

INTRODUCTION

This invention relates to an apparatus and method for rapidly determining the amount of volatile matter in a substance containing a polar material such as moisture. More particularly, the invention relates to an apparatus which quickly determines the percentage of volatiles in a given material by heat weight loss without accomplishing a total drying of the material. The projected final dry weight is determined after a short heat induction period which volatilizes some of the polar materials and projects the final dry weight based on a mathematical determination of the drying rate curve. The apparatus of the present invention performs these determinations including the percentage of volatiles in a given sample without operator assistance beyond the placing of the sample in the test apparatus.

BACKGROUND OF THE INVENTION

The determination of volatiles in a given substance is a very routine determination made countless times every day in numerous industries. Such tests are run on literally thousands of items ranging from agricultural products such as tests which determine the percentage of moisture in corn, wheat, oats, tobacco and the like to textiles, foods, films, coatings, paints, etc. Numerous industrial products and processes require testing to determine the percentage of volatiles, whether such volatiles be water, solvents or other diluents. These tests include the determination of the solid materials in paints, varnishes, lacquers, paper products, agricultural products and the like. Practically all items which are sold on a weight basis and are likely to absorb or contain moisture require correction for such gain or loss such that a customer is not charged for water or other diluent which might be in the particular material being sold. In the same manner, numerous items require a certain specified moisture or volatile level to be suitable for further use and are sold in the trade as being within specified ranges. Thus, considerable time is expended in quality control processes and tests to obtain the proper or desired percentage of moisture or solvent in the substance being processed or sold.

In a like manner, numerous industrial processes require constant determinations of moisture or solvent level as the product is being processed or manufactured. Consequently, industry and the trade has expended considerable efforts in the control and calculation of moisture and volatile content.

Previously, tests for determining the percentage of volatiles was conducted by typical weigh-dry-weigh analysis. The sample to be tested would first be weighed by an operator and then placed on a hot plate or in a vacuum oven for a predetermined period of time, normally on the order of 30 minutes to 4 hours. The sample would then be cooled, reweighed and a calculation made to determine the percentage of volatiles removed from the sample.

Another method used is known as the Karl Fischer determination. This test involved the titration with a specified chemical reagent and a subsequent calculation of the amount of moisture present based on the titration.

Such methods are time consuming and require operator skill. The accuracy of the test is often directly related to the skill and care exercised by the operator. Further, while such tests are largely repetitious, an operator is substantially limited in the number of tests which can be performed in a given period. In many instances, such as in quality control work, the time required for a signal test, i.e. as much as 2 hours or more, greatly inhibits plant operations such that processing conditions are normally two or more hours ahead of the test results. This requires advanced interpretation of processing conditions and estimations as to when the product is within specifications. Also, oven drying tends to drive off other volatile materials in addition to water. Thus, accuracy is often poor due to loss of other substances from the long drying times required.

In applicants' parent application noted above, an apparatus and method were described whereby volatiles in a sample material could be determined in a matter of minutes by means of an apparatus which automatically weighed the sample, volatilized the moisture and polar solvent by means of microwave heating and automatically calculated the weight loss and percent volatiles. While this determination was made within a matter of a few minutes, it has now been discovered that even faster determinations can be made, thereby making the present invention more suitable for inline computer processing control and other instances where even more rapid analysis is required. The present invention does not require the complete drying of the sample but rather determines the drying curve and mathematically projects the result after only a few minutes of drying induction time.

It is therefore an object of the present invention to provide an apparatus and process which automatically and rapidly determines the percentage of moisture or volatiles in a given substance in a fraction of the time previously required.

It is a further object of the present invention to provide an apparatus which projects the final dry weight of the sample without actually attaining complete dryness.

It is yet another object of the present invention to provide an apparatus and process which eliminates the possibility of overdrying of a sample.

It is yet another object of the present invention to provide an apparatus and process which can project moisture loss without the removal of other polar solvents if the same is not desired.

It is still another object of the present invention to provide a method which can be utilized in inline processing, such as in computer controlled processes, which require volatility measurements.

A further object of the present invention is to provide a method which eliminates the need for operator skill in determining the amount of volatiles in substances, reduces or eliminates the chance of human error and reduces the testing time to minutes or seconds per sample tested.

These and other objects will become apparent to those skilled in the art from the description of the invention which follows.

THE INVENTION

In accordance with the invention, an apparatus is provided for rapidly determining the volatiles in a substance containing a polar solvent comprising automatic weighing means, microwave heating means, apparatus controlling means and information readout means, said automatic weighing means being positioned within said microwave heating means, said apparatus controlling means being electrically connected to and preset to sequentially activate said weighing means and microwave heating means, said apparatus controlling means being further set to periodically sense said automatic weighing means a plurality of times and to produce an electrical output signal representative of said weight sensings, said apparatus controlling means further having means for projecting the anticipated weight change during said microwave heating to produce a further electrical output signal proportional to the anticipated weight change, said electrical output signals being electrically connected to said information readout means.

The preferred apparatus controlling means is a microprocessor based system comprising an analog to digital converter electrically connected to an input-output unit, a central processor unit and a read-only memory register for the storing of the preset sequencing means. The microprocessor is preset to sense the weight change during the initial period of drying and to mathematically project the final dry weight based on the sensed drying curve. Alternatively, the apparatus of our patent U.S. Pat. No. 3,909,598 can be modified as described heren to provide the apparatus and method of the present invention.

DETAILS OF THE INVENTION

The present invention is based upon the discovery that sample weight loss with time during microwave drying follows an exponential function after a short induction period of approximately 30 seconds. Since the weight loss with time can be described mathematically, it becomes possible to project the final dry weight while only partially drying the sample. The advantages of this technique include the ability to much more rapidly determine the percent of moisture and/or volatiles because the final weight can be projected in a much shorter interval of time than the time required for complete drying of the sample. For instance, with the drying time for complete dryness of 5 minutes, a final weight projection can be made within approximately 1 to 1½ minutes instead of the full drying time.

Additionally, the present method and apparatus provides for a more accurate determination of moisture. Because the sample is not being completely dried, the present apparatus and procedure eliminates the possibility of overdrying or removing polar materials which should not be removed for an accurate determination of the volatility.

The mathematical equations required for the calculation of the projected final weight loss have been determined. When these equations are used in conjunction with the appropriate apparatus controlling hardware and preset sequencing, the present invention is functional as described herein.

The invention will be more particularly described by reference to the drawings in which.

Figure 1:
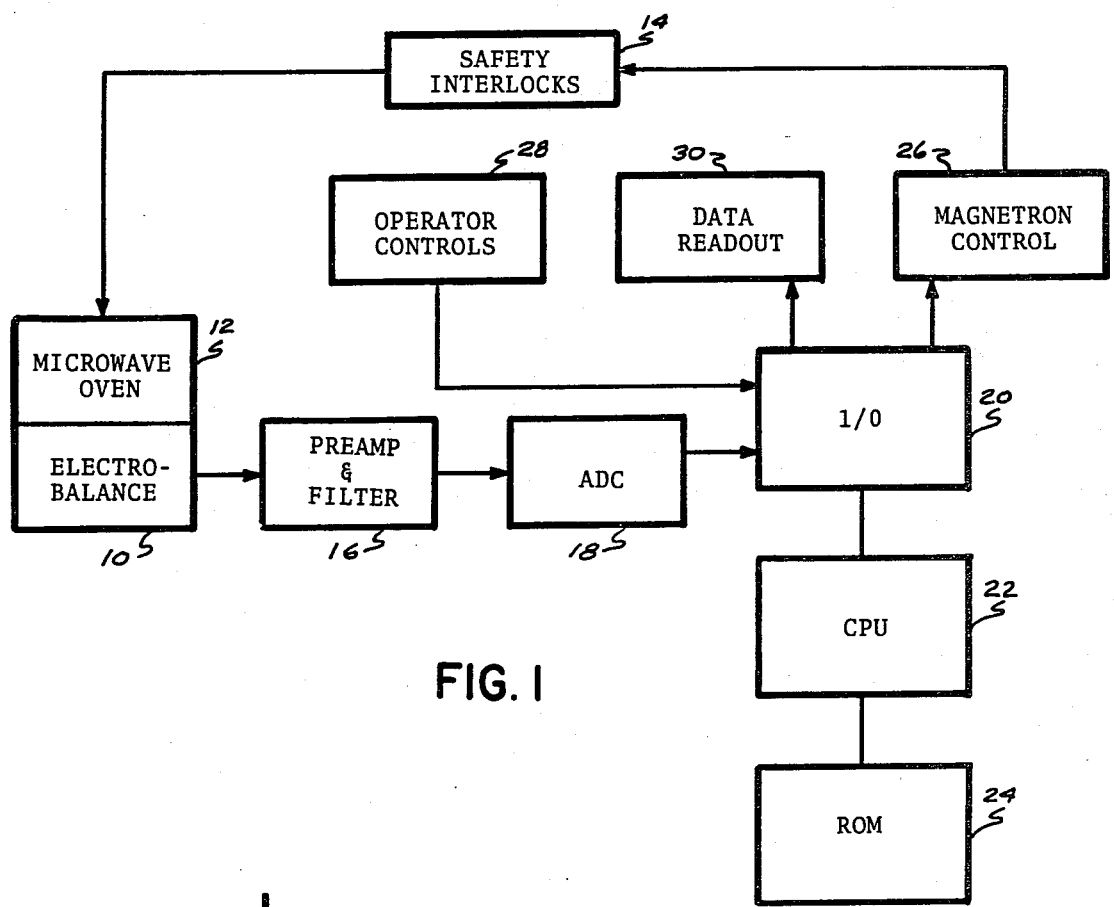
FIG. 1 is a schematic diagram of the preferred apparatus and steps in the method of the present invention and FIG. 2 is a graph which illustrates a typical microwave drying curve showing weight change with time during microwave heating.

Referring more particularly to FIG. 1, the apparatus and method of the present invention utilizes an automatic balance, preferably an electronic balance or other automatic balance means which can be equipped to give an electrical signal proportional to the measured weight. The automatic balance 10 is positioned within a microwave heating chamber or oven 12, such as is known in the art as a microwave oven. The preferred mode of positioning the weighing means utilizes a top loading electronic balance which projects through the floor of the microwave oven. The parts of the balance projecting into the microwave oven are preferably composed of materials which are transparent to the microwaves, thereby eliminating heating of the balance parts during the microwave heating phase. Typically, a polypropylene, Teflon, polycarbonates, polyester and the like plastics are used for the stem and balance plate. In certain uses wherein additional heat is desired to aid in drying the sample, heat generating parts such as a heat generating balance plate or sample container can be used. Glass is particularly suitable for this purpose because it normally has sufficient moisture trapped therein to generate heat when subjected to the noted microwave radiation.

The microwave oven may be of conventional design having proper radiation shielding. It is, however, particularly desirable to make certain modifications to such conventional ovens to improve the heating efficiency for the present use. First, it is desirable to utilize a radiation mixer to mix and disperse the radiation. Various radiation mixers are known in the art. Normally, they are rotating, fan-like machines which reflect the radiation. Such mixers avoid the production of hot spots which could decompose or destroy part of the sample being tested.

Secondly, it is particularly desirable to equip the oven with other radiation-absorbing materials or isolators. Radiation absorbing materials will couple with the radiation being emitted in the oven and thus prevent decomposition of the sample due to excessive radiation. By having a radiation coupling material present, the life of the magnetron is increased. Additionally, the coupling material helps in preventing leakage of radiation from the oven.

A preferred coupling material is water, although any other polar substance could be used. It is preferred to circulate the coupling material through the oven in radiation transparent tubing. The amount of coupling material used can thus be readily regulated and adjusted to the desired volume.

Rather than using a coupling material, a radiation isolator can be used. An isolator is a terminal circulator which absorbs reflected radiation and prevents a buildup of heat. Such devices are known in the art.

As is recognized in the art, microwave radiation is absorbed by water and polar organic molecules, causing an increase in molecular motion. Due to the absorption of radiation energy, the water and polar solvents are selectively heated and removed through heating and vaporization. It should also be noted that when a polar material is present, other nonpolar volatiles could be removed due to the heating effect of the polar material.

The operation of the apparatus is controlled by an apparatus control means and/or a data acquisition and control system which can be electronic analog circuitry, electronic switching, timing and converting, digital computer systems, analog computer systems or microprocessor based systems. In each of the noted systems, the apparatus control means senses the electrical signal emitted by the balance. This electrical signal is first preferably passed through a preamplifier and noise filter 16. The signal is amplified and extraneous electrical noise is filtered out.

The microprocessor based system is the preferred data acquisition and control means. It is comprised of three units known as I/O (input-output unit) 20, CPU (central processor unit) 22 and ROM (read only memory unit) 24, and preferably includes a fourth unit known as ADC (analog to digital converter) 18. The microprocessor controls the microwave oven by initiating magnetron control 26 through safety interlocks 14. The test is initiated via operator controls 28 which initiates the microprocessor to go through the program sequence culminating in data readout 30.

Referring more particularly to the microprocessor units, ADC 18 is preferably a conventional converter for high resolution ratiometric determinations utilizing the dual-slope principle. The ADC is used for converting an analog signal into binary bits and is utilized to control the sensing of the electronic balance signal to input-output control 20. I/O 20, CPU 22 and ROM 24 comprise the heart of the microprocessor. The noted items are conventionally available programmable logic systems known as a microcomputer set. These items basically receive information, process or interpret it and send it on in the form of data to be stored or instructions to be executed.

The microprocessor operates by receiving sequential binary coded information stored in addressable memory locations such as the ROM. Basically, the microprocessor needs to keep track of the program and where the data is stored in the ROM. It, therefore, needs its own memories, called registers. One memory, an instruction register, stores instructions to be executed, thus keeping the microprocessor informed as to what it is doing at any particular instant. A second memory performs the functions of a program counter-register, storing and then divulging the address of the next instruction to be read from the ROM. A third memory register called the accumulator provides a place to carry out the operation called for by the instruction.

A typical program logic system useful in the present invention is known as the Intel 4004 Micro Computer Set, available from Pro-Log Corporation of California.

Figure 2:
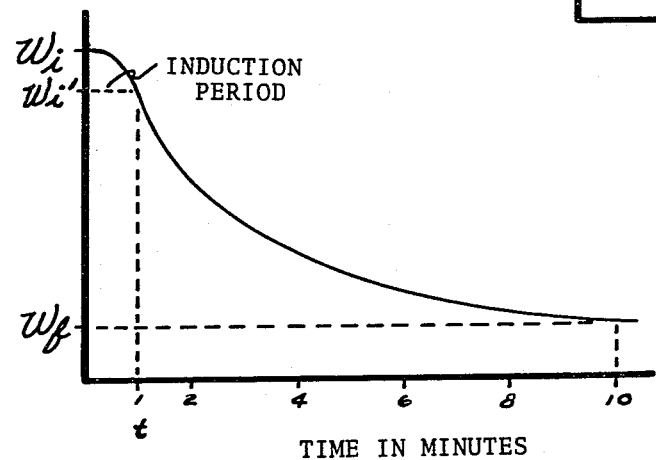
Figure 3:
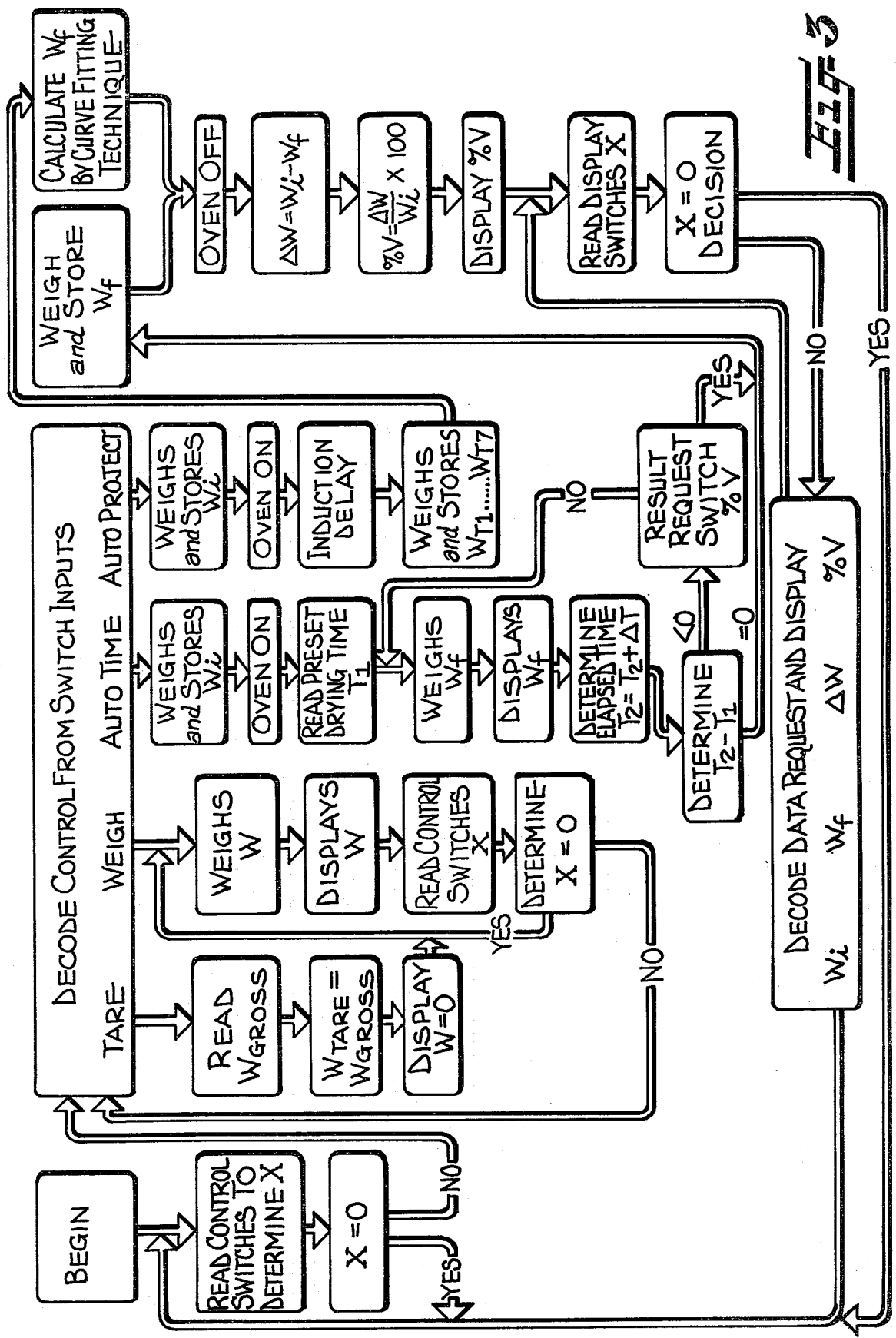
FIG. 3 is a schematic flow diagram of how the computer program functions in accordance with the embodiment more particularly set forth hereinafter.

The microprocessor is programmed in accordance with the invention to produce the desired results. Referring more particularly to FIG. 2, it has been determined that volatiles lost in a given test sample follow an exponential curve of the type shown in FIG. 2. In the graph shown there, $W_i$ indicates the initial sample weight, $W_i'$ the sample weight after an induction period of heating wherein volatiles have begun to be lost from the sample, and $W_f$ indicates the final sample weight. Drying time t is shown in minutes. As the microwave heating proceeds, there is a short period of about 30 seconds prior to the exponential weight loss in the sample. If $W_t$ represents the sample weight at a given time t, then the drying curve representing weight change in the sample is described by the mathematical equations:

$$w_f - w_t = (w_f - w_i')e^{-kt}$$

wherein e is the natural logarithm and k is a drying constant equal to B as determined below. t is equal to real time minus an induction period sufficient to place the point $w_i'$, t on the exponential curve of FIG. 2. Therefore, $w_i'$ is the sample weight at t equal to 0 whereas $w_i$ is the actual initial sample weight. Since $$\Delta t = t_2 - t_1$$

therefore $$w_{t2} - w_{t1} = (w_f - w_i')e^{-kt_1}(1 - e^{-k\Delta t})$$

and $$\ln(w_{t1} - w_{t2}) = \ln(w_i' - w_f) + \ln(1 - e^{-k\Delta t}) - kt_1$$
$$Y = A + BX$$

which is the equation of a straight line wherein $$Y = \ln(w_{t1} - w_{t2}) \text{ and } X = t_1$$

Solve for A and B using least square-fit:

$$A = \frac{\Sigma X^2 \Sigma Y - \Sigma X \Sigma XY}{n\Sigma X^2 - (\Sigma X)^2}$$

$$B = \frac{n\Sigma XY - \Sigma X \Sigma Y}{n\Sigma X^2 - (\Sigma X)^2}$$

wherein n equals the number of sample weights $$W_f = w_i' - \frac{e^A}{1 - e^{B\Delta t}}$$

$$\% \text{ Volatiles} = \left( \frac{W_i - W_i' + \frac{e^A}{1 - e^{B\Delta t}}}{W_i} \right) 100$$

To effect the weight change determination by the present procedure, the microprocessor is preset to make the above determinations by sensing the initial weight $W_i$, commence microwave heating and after a short induction heating time of say 10 to 60 seconds, begin sensing the weight of sample $W_t$ at periodic intervals of, for instance, 2 to 10 second intervals, thereby taking a series of weight measurements such as:

Seven weight measurements:

$W_1 \rightarrow 30$ seconds; $W_2 \rightarrow 40$ seconds; ... $W_7 \rightarrow 90$ seconds The microprocessor computes $\text{Ln}(W_{t1} - W_{t2})$ for each time interval. Using $\text{Ln}(W_{t1} - W_{t2}) = Y$ and $t_1 = X_1$. The microprocessor determines A and B using the above-noted least square equation. Having solved A and B, the final weight $W_f$ is projected using A and B values. Final weight $W_f$ can, of course, be converted to percent moisture or percent weight loss by the above-noted equation.

Alternatively, the microprocessor can be preset to sense weight change at a frequency of, say, every 0.1 to 10 seconds and compare said sensing using a delta t of 10 to 60 seconds such that $$Y = \ln(W_t - W_{t+\Delta t})$$

is determined. For example, wherein Δt equals 50 seconds and the frequency of sensing is set for 3 seconds after an induction period of 60 seconds, a plurality of data points are used to determine A and B accordingly:

$$Y_1 = \ln(W_{60} - W_{110}) \quad X_1 = t_1 = 0$$
$$Y_w = \ln(W_{63} - W_{113}) \quad X_2 = t_2 = 3$$
$$Y_3 = \ln(W_{66} - W_{116}) \quad X_3 = t_3 = 6$$
$$\text{etc} \ldots Y_6 = \ln(W_{75} - W_{125}) \quad X_6 = t_6 = 15$$

and Y is solved in accordance with the above equations to determine A and B.

With the known equations, the microprocessor of the present invention can be preset to determine the projected weight loss of the sample at complete drying without having actually completely dried the sample.

Alternatively, the apparatus of the present invention can be operated by electronic switching and/or analog circuitry which can perform the sequential activations of the apparatus and the determinations therefore. The programming of the microprocessor or other computer means is clearly apparent to those skilled in the programming art from the description of the process steps and the mathematical computations set forth herein. The particular program use will depend primarily on the computer means used and will follow the format set forth herein.

Referring again to FIG. 1, it will be seen that the testing sequence is initiated by an operator, such as by the pushing of a start button in operator controls 28 after having placed a sample to be tested on the electronic balance and closing the microwave oven.

The size of the sample can vary with the instrument size, electronic balance weight range and accuracy of the test results desired. The electronic balance and microwave oven is likewise sized for the intended usage. It should be noted that the basic usage of the present apparatus will be primarily for analytical purposes and, as such, analytical weight ranges and sizes are normally used. The apparatus is therefore best sized such that the sample will give at least about a 100 milligram weight loss for the preferred electronic balance. This means that with a material containing 5 percent moisture, the minimum sample size would preferably be about 2 grams. It is, of course, readily apparent that more sensitive electronic balances can be used for smaller samples, but such are generally impractical except for specialized usages. Therefore, the preferred sample weight will generally range between about 1 to 40 grams for most usages, depending on the amount of volatiles actually present. Weights up to about 1,000 grams or more can be used with proper sizing of the electronic balance.

Having initiated the tests, the microprocessor is programmed to periodically sense the electronic balance signal. This can be done at any desired interval from as little as a fraction of a second to 30-second intervals or longer. Normally, 10-second intervals after an initial induction period of about 30 seconds will provide a sufficiently accurate drying curve to produce the accuracy desired for most results. Of course, a greater number of weight sensing at shorter time intervals between sensings generally produces more accuracy in the projected curve while longer intervals between sensing lessens the accuracy of the projected curve.

The total time required for an accurate projection of final volatile loss depends largely upon the material being analyzed, the sample size and the volatility of the material being removed. The most preferred time is readily determined empirically and can vary considerably from as little as about 30 seconds to as long as about 10 minutes. The particular time required is largely dependent upon the radiation absorption coefficient of the particular volatile material and, since the sample is not dried to completeness, only that time which is sufficient to accurate compute the drying curve is required.

The oven magnetron is preferably of standard manufacture having a power output of 500 to 800 watts and a frequency within government approved ranges. Operator controls can be provided to vary the power of the magnetron. The United States Federal Communication Commission has designated the frequencies of 915 and 2450 megahertz as suitable for such magnetrons. Smaller magnetrons could be used with a corresponding limitation of versatility. Larger magnetrons could also be used but are generally unnecessary for normal analytical usage. In all instances, adequate radiation shielding is provided, as required by government regulations, along with safety interlocks to eliminate the possibility of radiation leaking from the oven.

Having completed the sequence as programmed in the microprocessor, information readout via data readout 30 is effected in readable form. Such data readout can be of any of the known forms of computer readout. Such forms include printed copy, digital panel meter readings, direct feed to other computers or to controlling processing mechanisms, and the like. A preferred mode of readout is the digital panel meter. Such meters used in conjunction with visible indicators, are particularly helpful in normal testing procedures. Indicators designated by code, numerals, lights or the like, signal the particular readout being shown on the digital panel meter. Such readouts can include initial sample weight, sample weight at time t, final sample weight, the difference between initial and final weight and the percent weight loss or percent volatiles in the sample.

It is preferred that operator controls 28 have memory recall such that any one or more of the noted measurements can be recalled. Such recall is useful where the operator may want to recheck the initial weight and weight changes to check calculations. Push buttons or electrical switches can be provided so that the operator can reexamine these data on the digital panel meter. Where desired, printed readout can also be utilized and when used, such recall is not necessary since the readout is on printed copy.

In the operation of the present apparatus, the repushing of the operator control start button erases the previous memory units from previous tests and reinitiates a new testing sequence.

While the present apparatus and method has been described more particularly as an analytical instrument, it is recognized that this apparatus and method can be readily adopted for other uses such as in-line production control, production usage and the preparation of dried samples for further testing and other uses, as may be required in various commercial and industrial processing. Consequently, the present invention is not intended to be limited except as noted in the appended claims.

What is claimed is:

1. An apparatus for measuring the volatile content of substances comprising electronic weighing means, microwave heating means including an enclosed heating chamber and a microwave energy source transmittably connected therewith, data acquisition and apparatus control means and information readout means, said electronic weighing means being at least partially positioned within said microwave heating means, said apparatus control means being electrically connected to and preset to sequentially actuate said weighing means and microwave heating means, said data acquisition and apparatus control means being further set to periodically sense said electronic weighing means a plurality of times and to provide an electrical output signal representative of said weight sensing, said data acquisition and apparatus control means further having means for projecting the anticipated weight change during said microwave heating to produce a further electrical output signal proportional to the anticipated weight change, said electrical output signals being electrically connected to said information readout means.

2. The apparatus of claim 1 wherein the data acquisition and apparatus control means are electronic analog circuitry.

3. The apparatus of claim 1 wherein the data acquisition and apparatus control means is a computer.

4. The apparatus of claim 3 wherein the computer is a microprocessor based acquisition and control system.

5. The apparatus of claim 4 wherein the microprocessor based system comprises an electrically connected input-output unit, a central processor unit and a read-only memory unit.

6. The apparatus of claim 1 wherein an analog to digital converter is electrically interposed between said electronic weighing means and said apparatus control means.

7. The apparatus of claim 1 wherein said information readout means is electrically connected to process control means or computer means.

8. The apparatus of claim 1 wherein said information readout means is visible printout or digital meter means.

9. The apparatus of claim 8 wherein the magnetron wattage can be reduced to a lower output.

10. The apparatus of claim 1 wherein said microwave heating means is a magnetron radiation tube of 500 to 800 watts.

11. The apparatus of claim 1 wherein the microwave heating means has a radiation absorber associated therewith.

12. The apparatus of claim 11 wherein the radiation absorber is a terminal circulator.

13. The apparatus of claim 11 wherein the radiation absorber is a water loop.

14. The apparatus of claim 1 wherein the microwave heating means has a radiation isolator associated therewith.

15. The apparatus of claim 14 wherein the isolator is a terminal circulator for absorption of reflected radiation.

16. A method for rapidly determining the amount of volatiles in a substance containing volatiles comprising placing a sample of the substance to be measured on an electronic balance, subjecting said substance to microwave heating, periodically repeatedly sensing the weight of said substance a plurality of times during said microwave heating, determining the exponential weight-loss curve based on said plurality of weight sensings and projecting the final weight of said sample based on said determined exponential curve.

17. The method of claim 16 wherein a microwave heating induction period of from about 1 to 120 seconds is used prior to determining the exponential weight-loss curve.

18. The method of claim 16 wherein the periodic sensing of weight loss is at a frequency of every 0.1 to 60 seconds.

19. The method of claim 18 wherein the periodic sensing of weight utilizes weight differential sensing according to the formula $\ln(W_t - W_{t+\Delta t})$ wherein W is the weight at time t and $\Delta t$ is equal to 10 to 60 seconds.

20. The method of claim 16 wherein the exponential curve is computed according to the formula $$\ln(w_{t1} - w_{t2}) = \ln(w'_i - w_f) + \ln(1 - e^{-k\Delta t}) - kt_1$$

$$Y \quad = \quad A \quad + BX$$

21. The method of claim 20 wherein A and B are determined using the least square fit.

22. The method of claim 21 wherein the percent volatiles are determined according to the equation $$\left( \frac{W_i - W'_i + \dfrac{e^A}{1 - e^{B\Delta t}}}{W_i} \right) 100$$

23. A method for use in determining volatile content of a sample comprising the steps of:
(a) weighing said sample to obtain the weight thereof; then
(b) heating said sample; and
(c) during the course of such heating of said sample, weighing said sample
  (1) at a first time spaced from the start of such heating course by a first predetermined measure of time, and
  (2) at a plurality of subsequent times, said subsequent times beginning with an initial time spaced by a second predetermined measure of time from said first time and each being uniformly spaced one from the other by said second predetermined measure of time; and
(d) obtaining differences between said weights obtained in said step (c) which are taken at times separated from one another by a measure of time which is an integral multiple of said second predetermined measure, said steps (c) and (d) being controlled and scheduled by a computer.

24. The method claimed in claim 23 including the further step, controlled and scheduled by a computer, of determining natural logarithms of such weight differences and identifying characteristics of a linear relationship between such natural logarithms and selected of said step (c) times.

25. The method claims in claim 24 wherein said identifying of said linear relationship is controlled and scheduled by a computer and obtained by determining least squares fit of said natural logarithms and said selected step (c) times.

26. The method claims in claim 25 including the further steps, controlled and scheduled by a computer, of determining slope and intercept values defining said linear relationship.

27. The method claimed in claim 26 wherein said volatile content is determined, under control and scheduling by a computer, as a function of said weight differences, said weight obtained in said step (a) and such determined slope.

28. The method claimed in claim 26 wherein said volatile content is determined, under control and scheduling by a computer, as a function of said weight obtained in said step (a), such determined slope, such determined intercept and said integral multiple of said second predetermined measure.

29. The method claimed in claim 26 wherein said volatile content is determined, under control and scheduling by a computer, as a function of said weight differences, said weight obtained in said step (a) and such determined slope and further as a function of said weight obtained in said step (a), such determined slope, such determined intercept and said integral multiple of said second predetermined measure.

30. The method claimed in claim 23 wherein said sample is tobacco and said volatile content is water.

* * * * *